United States Patent [19]

Meienhofer

[11] 3,960,828
[45] June 1, 1976

[54] CATALYTIC HYDROGENOLYSIS OF PROTECTED SULFUR CONTAINING PEPTIDES

[75] Inventor: Johannes Arnold Meienhofer, Upper Montclair, N.J.

[73] Assignee: The United States of America as represented by the Department of Health, Education and Welfare, Washington, D.C.

[22] Filed: Mar. 20, 1974

[21] Appl. No.: 453,141

[52] U.S. Cl. .................. 260/112.5 R; 260/306.7 R; 260/534 S
[51] Int. Cl.² .................. C07C 103/52; C07G 7/00
[58] Field of Search ............. 260/112.5, 470, 481 R, 260/516, 534 S, 690

[56] References Cited
OTHER PUBLICATIONS

DuVigneaud et al.: J. Am. Chem. Soc., 52, 4500–4504, (1930).

Doyle et al.: J. Chem. Soc., 1440–1444, (1962).

DeHaas et al.: Rec. Trav. Chim. Pays-Bas, 81, 215–218, (1962).

Berse et al.: J. Org. Chem., 22, 805–808, (1957).

Primary Examiner—Lewis Gotts
Assistant Examiner—Reginald J. Suyat
Attorney, Agent, or Firm—John S. Roberts, Jr.; Norman J. Latker; Thomas G. Ferris

[57] ABSTRACT

The use of catalytic hydrogenolysis to selectively deblock protected moieties in sulfur containing compounds has not been a practical process due to poisoning of the catalyst by the sulfur compound. It has now been found that catalytic hydrogenolysis of sulfur compounds can be successfully carried out by conducting the reaction in liquid ammonia as solvent.

6 Claims, No Drawings

CATALYTIC HYDROGENOLYSIS OF PROTECTED SULFUR CONTAINING PEPTIDES

The invention described herein was made in the course of work under a grant or award from the Department of Health, Education and Welfare.

BACKGROUND OF THE INVENTION

High selectivity of cleavage and general applicability to all commonly occurring amino acids are important criteria in choosing useful combinations of main chain and side chain protecting groups in peptide synthesis. The most selective procedure available to date has been catalytic hydrogenolysis of $N^\alpha$-benzyloxycarbonyl (Z) groups in peptides whose side chain functions have been protected by t-butyl ester, t-butyl ether and/or t-butyloxycarbonyl (Boc) groups which completely resist hydrogenolysis. However, this excellent system has not been generally applicable since catalytic hydrogenolysis failed with cysteine or methionine containing peptides due to catalyst poisoning.

There have been attempts to overcome this restriction by resorting to various expedients. Examples of such expedients include the addition of a tertiary base (Acta Chim. Acad. Sci. Hung., 45, 15 (1965); 50, 339 (1966)) or of boron trifluoride etherate (Chem. Pharm. Bull., 16, 1342 (1968), to the hydrogenolysis reaction medium. Another suggested technique involves the use of the N -1,1-dimethyl-2-propynyloxycarbonyl group (J. Amer. Chem. Soc., 93, 3302 (1971)) which may be hydrogenolized with partially poisoned catalysts. In no case, however, has it been possible to achieve the desired levels of selective deblocking and high end product yields with these techniques.

It is further known in the art to employ liquid ammonia as a solvent for many amino acid derivatives and protected peptides some of which are not readily soluble in other solvents. See, for example, the papers by du Vigneaud et al. in J. Amer. Chem. Soc. 52, 4500 (1930) and 75, 3879 (1953).

DESCRIPTION OF THE INVENTION

The present invention relates to the discovery that compounds containing sulfur and having substituent groups which are labile to hydrogenolysis can be successfully hydrogenolyzed by utilizing liquid ammonia as the reacton medium. Due to this discovery it is now possible to selectively cleave off benzyloxycarbonyl groups substituted on amino or oxy functionalities in sulfur containing compounds as well as cleaving groups such as benzyl esters and benzyl ethers. It is also within the scope of this invention to hydrogenolyze the mono- or di- alkoxy, alkyl, halo or nitro substituted benzyl derivatives of those groups just mentioned. Still another protective group which can be selectively cleaved herein is the nitro group such as in nitroarginine.

Thus the present process can be utilized most effectively in treating sulfur containing amino acids or peptides which have at least one protective group which is labile to hydrogenolysis. Suitable substrates upon which this process can be employed include such sulfur containing amino acids or derivatives such as cysteine, homocysteine, methionine, penicillamine, thiazolidine and other related compounds; intermediates for the synthesis of penicillin and analogs or derivatives thereof; intermediates for the synthesis of insulin; intermediates for the synthesis of ACTH; intermediates for the synthesis of calcitonin; intermediates for the synthesis of growth hormone, somatostatin; and the like. Other uses include the modification of biologically active sulfur containing proteins, such as enzymes, by the reduction of disulfide bonds. Still other similar uses would suggest themselves to those skilled in the art.

The catalyst used in the instant hydrogenolysis process is palladium, most preferably in the form of palladium black. It is also possible to utilize supported palladium catalysts such as palladium on charcoal, barium sulfate, or any other support conventionally used for palladium in the catalytic art. For most purposes the palladium catalyst is used in a concentration of about 0.1 g. to about 1.0 g. of palladium per mmole of substrate, most preferably in the range of about 0.2 to 0.5 g/mmole. It is understood however, that the catalyst concentration is not narrowly critical and larger or smaller amounts may be used in appropriate situations.

Suitable process parameters for the catalytic hydrogenolysis of this invention include a temperature in the range of about $-33°$ to about $-70°C$. most preferably at the reflux temperature of liquid ammonia ($-33°C$.) with pressure of one atmosphere; at higher pressures such as for example 10 atmospheres in a sealed container the process may be conducted at room temperature or even higher.

The concentration of substrate depends on the solubility of the substrate in liquid ammonia but generally it is desirable to utilize concentrations of 50 to 150 ml. of liquid ammonia per mmole of substrate.

The hydrogen flow rate in the open system employed in the preferred embodiment of the process is not narrowly critical and will desirably be in the in the range of 5–50 ml/minute. Determination of the reaction end point can be conveniently done by following the reaction using thin-layer chromatography or other standard analytical procedures.

In the alternative embodiment the process is conducted under pressure in a sealed pressure bomb using the hydrogen uptake rate as the determinative factor in ascertaining the end point.

To maximize yield it is preferred in both of the above embodiments to keep the reaction mixture in an agitated condition by constant stirring or shaking of the reaction vessel.

The present process has been found to be especially useful to the synthesis of cysteine or methionine containing peptides utilizing $N^\alpha$-benzyloxycarbonyl as the labile protective group and t-butyl derivatives as the stable side chain protective group.

Model tests were conducted to determine the lability or stability of various protective groups to the hydrogenolysis process conditions of the preferred embodiment of this invention. Completely cleaved were benzyl ester, benzyl ether, 2,6-dichlorobenzyl ether, N-benzyloxycarbonyl, N-2-bromobenzyloxycarbonyl, N-4-methoxy-benzyloxycarbonyl and the nitro group of nitroarginine. Complete stability toward catalytic hydrogenolysis in liquid ammonia was shown by t-butyl ester, t-butyl ether, N-t-butyloxycarbonyl, N-p-toluenesulfonyl, S-benzyl and S-acetamidomethyl groups.

The process of the present invention is further illustrated by the following examples which demonstrate the synthesis of oxytocin via incremental chain elongation. Several of the described intermediates are novel compounds and are considered part of the instant invention.

The following is a general procedure for catalytic hydrogenolysis in liquid ammonia.

All glassware was dried prior to use. Anhydrous ammonia was passed through a drying tube filled with KOH pellets and condensed in a three-neck round bottom flask immersed in dry ice-acetone. The cold bath was removed and the flask fitted with a magnetic stirrer. A dry ice reflux condenser was placed on the center neck. $N^\alpha$-Benzyloxycarbonyl peptide derivative (1 mmol in approximately 150 ml.) was dissolved with stirring. Freshly prepared palladium black (0.2–0.5 g.), freed from water by thorough washing with anhydrous methanol, as added in methanol-wet form under a nitrogen barrier. A stream of dried (conc. $H_2SO_4$) hydrogen was continuously passed through the magnetically stirred solution at the boiling point of ammonia (ca −33°). Reaction progress was followed by thin layer chromatography. After 6–8 hrs., the ammonia was evaporated to dryness under nitrogen. The residue was immediately dissolved in distilled dimethylformamide or methanol and the solution filtered from the catalyst. Evaporation afforded products which were in most cases homogeneous.

EXAMPLE 1

S-benzyl-L-cysteinyl-L-prolyl-L-leucyl-glycinamide

S-Benzyl-N-benzyloxycarbonyl-L-cysteinyl-L-prolyl-L-leucyl-glycinamide (300 mg.) was dissolved in 35 ml. of anhydrous liquid ammonia and hydrogenated in the presence of freshly prepared palladium black (ca 0.1g.) and triethylamine (0.28 ml.) at the boiling point of the solvent. The reaction was followed by thin layer chromatography (solvent system $CCl_4/CH_3OH/CH_3COOH$ 8:1:1) which showed incomplete reaction (50–60%) after 6 hours. Evaporation of ammonia under nitrogen was followed by addition of methanol (10 ml.) and stirring for 10 min. The catalyst was then removed by filtration and washed with methanol (10 ml.). The combined filtrate and washings were passed through a column (1.2 × 10 cm) of Dowex 50 × 8 ($H^+$ form) which was washed with methanol. The desired material was then eluted with 2N ammonium hydroxide-methanol (1:1) and the eluate evaporated in vacuo. Crystallization from water gave 95.2 mg. (42.3%); m.p. 130°–134°.

EXAMPLE 2

L-asparaginyl-S-benzyl-L-cysteinyl-L-prolyl-L-leucyl-glycinamide

Benzyloxycarbonyl-L-asparaginyl-S-benzyl-L-cysteinyl-prolyl-L-leucylglycinamide (5.37 g., 7.40 mmol) was hydrogenated for 8 hr. in liquid ammonia (800 ml.) using methanol-wet palladium black as described in the general procedure to afford colorless crystals from methanol-ether, 4.36 g. (99%); m.p. 102°–104° with softening at 86°; $[\alpha]^{21}D/-59.1°$(c 1, dimethylformamide).

Anal. Calcd. for $C_{27}H_{41}N_7O_6S$ (591.7): C, 54.8; H, 6.98; N, 16.6; S, 5.42.

Found: C, 54.6; H, 7.25; N, 16.4; S, 4.99.

The starting material may be prepared as follows:

To a solution of S-benzyl-L-cysteinyl-L-prolyl-L-leucyl-glycinamide (0.502 g.) in ethyl acetate (3 ml.) benzyloxycarbonyl-L-asparagine p-nitrophenyl ester (0.387 g., 1.0 mmol) was added and the suspension stirred at room temperature for 48 hr. The precipitate which formed was collected by filtration and washed with ethyl acetate (20 ml.) and ethanol (5 ml.), and then dried. The crude benzyloxycarbonyl-L-asparaginyl-S-benzyl-L-cysteinyl-L-prolyl-L-leucyl-glycinamide was recrystallized from 40% methanol. Yield, 0.718 g. (99%); m.p. 212°–213.5°; $[\alpha]^{20}D$ −60.5° (c 1, dimethylformamide).

EXAMPLE 3

L-Glutaminyl-L-asparaginyl-S-benzyl-L-cysteinyl-L-prolyl-L-leucyl-glycinamide

Benzyloxycarbonyl-L-glutaminyl-L-asparaginyl-S-benzyl-L-cysteinyl-L-prolyl-L-leucyl-glycinamide (3.82 g, 4.47 mmol) was hydrogenated in liquid ammonia (600 ml.) for 6.5 hr. to give a colorless powder from methanol-ether. 3.25 g. (100%) m.p. 136°–138°; $[\alpha]^{21}D/-57.0°$ (c 1, dimethylformamide).

EXAMPLE 4

L-isoleucyl-L-glutaminyl-L-asparaginyl-S-benzyl-L-cysteinyl-L-prolyl-L-leucyl-glycinamide 4.11 g. (4.26 mmol) of benzyloxycarbonyl-L-isoleucyl-L-glutaminyl-L-asparaginyl-S-benzyl-L-cysteinyl-L-prolyl-L-leucyl-glycinamide was hydrogenated in liquid ammonia (600 ml.) for 8.5 hr. to produce colorless crystals from methanol-ether, 3.51 g. (99%); m.p. 218°–220° with softening at 168°; $[\alpha]^{21}D/-59.1°$ (c 1, dimethylformamide). The starting material may be prepared as follows:

The protected heptapeptide benzyloxycarbonyl-L-isoleucyl-L-asparaginyl-S-benzyl-L-cysteinyl-L-prolyl-L-leucyl-glycinamide was prepared by the coupling of the product of Example 3 with benzyloxycarbonyl-L-isoleucine p-nitrophenyl ester in 100% yield, m.p. 232°–233°; $[\alpha]^{21}D/-50.2°$ (c 1, dimethylformamide).

EXAMPLE 5

L-Tyrosyl-L-isoleucyl-L-glutaminyl-L-asparaginyl-S-benzyl-L-cysteinyl-L-prolyl-L-leucyl-glycinaide Z-Tyr-Ile-Gln-Asn-Cys(Bzl)-Pro-Leu-Gly-$NH_2$ (3.39 g., 3.0 mmol) was hydrogenated in liquid ammonia (500 ml.) for 8 hr. Colorless crystals were obtained from methanol-ether, 4.21 g. (100%); m.p. 179°–180°; $R_f$ 0.55; $[\alpha]^{21}D/-41.3°$ (c 1, dimethylformamide).

Anal. Calcd. for $C_{47}H_{69}N_{11}O_{11}S$ (996.2): C, 56.7; H, 6.98; N, 15.5; S, 3.22.

Found: C, 57.0; H, 6.62; N, 15.2 S, 2.88.

The starting material may be prepared as follows:

The product of Example 4 was coupled with benzyloxycarbonyl-L-tyrosine p-nitrophenyl ester in the usual manner to afford the protected octapeptide, Z-Tyr-Ile-Gln-Asn-Cys(Bzl)-Pro-Leu-Gly-$NH_2$ in 82.4% yield, m.p. 237°–238.5°; $R_f$ 0.02, 0.66; $[\alpha]^{21}D/-43.0°$ (c 1, dimethylformamide).

EXAMPLE 6

S-Benzyl-L-cysteinyl-L-tyrosyl-L-isoleucyl-L-glutaminy-L-asparaginyl-S-benzyl-L-cysteinyl-L-prolyl-L-leucyl-glycinamide Hydrogenation of Z-Cys(Bzl)-Tyr-Ile-Gln-Asn-Cys(Bzl)-Pro-Leu-Gly-$NH_2$ (52 mg.) in liquid ammonia (20 ml.) was carried out for 8 hr. in the presence of palladium catalyst. Colorless crystals were obtained from ethanol, 44.1 mg. (94.5%); m.p. 244°–246° with softening at around 175°; $[\alpha]^{21}D/-48.8°$ (c 0.5, dimethylformamide).

Anal. Calcd. for $C_{57}H_{80}N_{12}O_{12}S_2$ (1189.5): C, 57.6; H, 6.78; N, 14.1; S, 5.39.

Found: C, 57.8; H, 6.62; N, 14.1; S, 5.83.

The starting material may be prepared as follows:

Condensation of the product of Example 5 with N-benzyloxycarbonyl-S-benzyl-L-cystein-p-nitrophenyl ester afforded the protected nonapeptide Z-Cys(Bzl)-Tyr-Ile-Gln-Asn-Cys(Bzl)-Pro-Leu-Gly-NH$_2$ in 98% yield as colorless microscopic needles from dimethylformamide-formic acid (99:1), m.p. 235°–236.5°; $[\alpha]^{21}D/-58.2°$ (c 2.5 acetic acid).

EXAMPLE 7

Conversion of the protected nonapeptide Z-Cys(Bzl)-Tyr-Ile-Gln-Asn-Cys(Bzl)-Pro-Leu-Gly-NH$_2$ (250 mg.) to oxytocin was conducted according to known procedures. Reduction with sodium in liquid ammonia, evaporation of the solvent under a stream of dry oxygen-free nitrogen, dissolving of the residue in freshly distilled deaerated water (pH 6.8), oxidation with 0.02M potassium ferricyanide, column chromatography on Dowex 2 × 8, countercurrent distribution in n-butanol-n-propanol - 0.05% acetic acid (2:1:3), and Sephadex G-25 gel filtration followed by lyophilization yielded highly active oxytocin (92 mg. 48%) possessing approximately 470 IU/mg of oxytocic potency.

I claim:

1. A process for the catalytic hydrogenolysis of sulfur containing peptide compounds also containing a benzyloxycarbonyl protective group labile to hydrogenolysis and additionally containing one or more protective groups which are stable to hydrogenolysis which process comprises reacting said sulfur compounds with hydrogen in the presence of palladium catalyst in a liquid ammonia solvent medium.

2. The process of claim 1 wherein said sulfur containing peptides contain at least one residue of the group consisting of cysteine, homocysteine, methionine, penicillamine and thiazolidine.

3. The process of claim 1 wherein said stable protective group is selected from the group consisting of t-butyl ester, t-butyl ether, N-t-butyloxycarbonyl, N-p-toluenesulfonyl, S-benzyl and S-acetamidomethyl.

4. The process of claim 1 wherein the process is conducted in an open system and at a temperature in the range of from about −33 to −70°C.

5. The process of claim 1 wherein the process is conducted in a closed system, at elevated pressures and at a temperature of about room temperature.

6. The process of claim 1 wherein the said palladium is in the form of palladium black.

* * * * *